(12) United States Patent
Nguyen et al.

(10) Patent No.: US 7,449,029 B2
(45) Date of Patent: Nov. 11, 2008

(54) COMPOSITION AND PROCESS FOR COLOR HAIR

(75) Inventors: Nghi Van Nguyen, Edison, NJ (US); David W. Cannell, Plainfield, NJ (US); Cynthia Chong Espino, Princeton, NJ (US); Katherine Natalie Barger, Cranford, NJ (US)

(73) Assignee: L'Oreal (FR)

( * ) Notice: Subject to any disclaimer, the term of this patent is extended or adjusted under 35 U.S.C. 154(b) by 370 days.

(21) Appl. No.: 11/280,372

(22) Filed: Nov. 16, 2005

(65) Prior Publication Data

US 2007/0107142 A1      May 17, 2007

(51) Int. Cl.
*A61Q 5/10* (2006.01)

(52) U.S. Cl. .............. 8/405; 8/406; 8/407; 8/426; 8/435; 8/551; 8/552; 8/581; 8/584; 132/202; 132/208

(58) Field of Classification Search .............. 8/405, 8/406, 407, 426, 435, 551, 552, 581, 584; 132/202, 208
See application file for complete search history.

(56) References Cited

U.S. PATENT DOCUMENTS

| | | | |
|---|---|---|---|
| 5,070,171 A | 12/1991 | O'Lenik, Jr. | |
| 5,093,452 A | 3/1992 | O'Lenik, Jr. | |
| 5,149,765 A | 9/1992 | O'Lenik, Jr. | |
| 5,248,783 A | 9/1993 | O'Lenik | |
| 5,739,371 A | 4/1998 | O'Lenik, Jr. | |
| 6,685,926 B2 | 2/2004 | Hehner et al. | |
| 6,770,103 B2 * | 8/2004 | Patel et al. ............. | 8/405 |
| 2003/0165453 A1 * | 9/2003 | Nguyen et al. ......... | 424/70.12 |

FOREIGN PATENT DOCUMENTS

| | | |
|---|---|---|
| DE | 197 35 865 | 4/1999 |
| EP | 1 238 648 | 9/2002 |
| EP | 1 302 195 | 4/2003 |
| EP | 1 312 341 | 5/2003 |
| EP | 1 402 881 | 3/2004 |
| EP | 1 733 717 | 12/2006 |
| WO | WO-93/25179 | 12/1993 |

OTHER PUBLICATIONS

CTFA International Cosmetic Ingredient Dictionary and Handbook, 8th ed. vol. 2, 2000, pp. 1701-1703.

* cited by examiner

*Primary Examiner*—Eisa B Elhilo
(74) *Attorney, Agent, or Firm*—Lerner, David, Littenberg, Krumholz & Mentlik, LLP

(57) ABSTRACT

A composition, kit and process for dyeing hair fibers in a manner which inhibits color loss during subsequent shampooing involving contacting the hair fibers with a composition containing: (a) at least one polyamine having at least two amino groups; (b) at least one anionic silicone; and (c) at least one dye component chosen from a direct dye and an oxidation dye, and wherein the dyed hair fibers inhibit color loss resulting from subsequent shampooing of the dyed hair fibers.

19 Claims, No Drawings

COMPOSITION AND PROCESS FOR COLOR HAIR

BACKGROUND OF THE INVENTION

The present invention relates to a composition and process for coloring hair. There are essentially two ways in which hair fibers may be dyed: "permanent" dyeing and "semi-permanent" dyeing.

The first, also known as oxidation dyeing, uses "oxidation" dye precursors, which are colorless or weakly colored compounds. Once mixed with oxidizing products, at the time of use, these precursors lead to colored compounds and dyes via a process of oxidative condensation. In this case, the colorations obtained are generally very colorfast and strong.

The second, also known as direct dyeing, uses direct dyes, which are nonionic or ionic dyes and colored compounds capable of producing a more or less pronounced change of the natural color of the hair, resistant to shampoo-washing several times. These dyes may or may not be used in the presence of an oxidizing agent.

In contrast with oxidation dye precursors, a direct dye is a relatively voluminous molecule that does not penetrate easily into the core of the fiber. Consequently, even though considerable progress has been made in this field, the phenomenon of bleeding of the coloration, i.e., color loss, during shampooing is still non-negligible, even if the dye(s) used is (are) chosen from cationic species. Moreover, the use of certain cationic direct dyes may be reflected by a reduction in the working qualities of the shampoos used after coloration, especially as regards the duration of the lather.

While the phenomenon of bleeding of the coloration during shampooing is more pronounced when direct dyes are used, this phenomenon occurs when oxidation dye precursors are employed as well.

Thus, one object of the present invention is to provide a composition and process for dyeing hair in a manner which inhibits color loss resulting from subsequent shampooing of the dyed hair fibers.

SUMMARY OF THE INVENTION

In order to achieve these and other advantages, the present invention is drawn to a hair dyeing composition containing:
(a) at least one polyamine compound having at least two amino groups;
(b) at least one anionic silicone; and
(c) at least one dye component chosen from a direct dye and an oxidation dye.

The present invention is also directed to a process for dyeing hair fibers in a manner which inhibits color loss resulting from subsequent shampooing, involving contacting hair fibers with the above-disclosed hair dyeing composition.

DETAILED DESCRIPTION

Other than in the operating examples, or where otherwise indicated, all numbers expressing quantities of ingredients and/or reaction conditions are to be understood as being modified in all instances by the term "about".

"Amino groups" as defined herein includes primary amino groups, secondary amino groups, and tertiary amino groups, and further includes amino groups which are terminal, pendant, and intercalated in a skeleton of the at least one polyamine compound, but does not, for example, include quaternary amino groups, amido groups, imino groups, nitrilo groups, or heteroatom analogs of any of the foregoing.

"At least one" as used herein means one or more and thus includes individual components as well as mixtures/combinations.

"Color loss" as defined herein refers to the phenomenon of bleeding of the coloration during shampooing.

The at least one polyamine compound of the present invention comprises at least two amino groups, preferably at least three amino groups, more preferably at least four amino groups, more preferably at least five amino groups, more preferably at least six amino groups, more preferably at least seven amino groups, more preferably at least eight amino groups, more preferably at least nine amino groups, and more preferably at least ten amino groups.

In one embodiment of the present invention, the at least one polyamine compound may, for example, be chosen from aminated polysaccharides comprising at least two amino groups, such as, for example, hydrolysates of aminated polysaccharides comprising greater than two amino groups. In one embodiment, the at least one polyamine compound may, for example, be chosen from polymers. Suitable polymers for use as the at least one amine compound are polymers comprising at least two amino groups as defined herein. Non-limiting examples of suitable polymers include homopolymers comprising at least two amino groups, copolymers comprising at least two amino groups, and terpolymers comprising at least two amino groups. Thus, the at least one polyamine compound comprising at least two amino groups may be chosen from, for example, polymers comprising at least two amino groups formed from (i) at least one monomer unit comprising at least one amino group as defined herein, and, optionally, (ii) at least one additional monomer unit different from the at least one monomer (i); and polymers comprising at least two amino groups formed from (i) at least one monomer comprising at least two amino groups as defined herein, and, optionally, (ii) at least one additional monomer unit different from the at least one monomer (i). According to the present invention, the at least one additional monomer different from the at least one monomer (i) may or may not comprise at least one amino group as defined herein. A particularly preferred polyamine polymer is chitosan.

In one embodiment of the present invention, the at least one polyamine compound is chosen from polyamines. As used herein, "polyamines" comprise at least two repeating units, wherein each unit comprises at least one amino group as defined herein. In one embodiment, polyamines are chosen from polyethyleneimines. Polyethyleneimines suitable for use in the compositions of the present invention may optionally be substituted. Non-limiting examples of polyethyleneimines which may be used in the composition according to the present invention are the Lupasol™ products commercially available from BASF. Suitable examples of Lupasol™ polyethyleneimines include Lupasol™ PS, Lupasol PL, Lupasol™ PR8515, Lupasol™ G20, Lupasol™ G35 as well as Lupasol™ SC® Polythyleneimine Reaction Products (such as Lupasol™ SC-61B®, Lupasol™ SC-62J®, and Lupasol™ SC-86X®). Other non-limiting examples of polyethyleneimines which may be used in the composition according to the present invention are the Epomin™ products commercially available from Aceto. Suitable examples of Epomin™ polyethyleneimines include Epomin™ SP-006, Epomin™ SP-012, Epomin™ SP-018, and Epomin™ P-1000.

Polyamines suitable for use in the present invention may also be chosen from polyvinylamines. Examples thereof include Lupamines® 9095, 9030, 9010, 5095, 1595 from BASF.

The polyamine compounds can also be substituted. An example of such a compound is PEG-15 Cocopolyamine from Cognis.

In another embodiment, the at least one polyamine compound comprising at least two amino groups is chosen from proteins and protein derivatives. Non-limiting examples of suitable proteins and protein derivatives for use in the present invention include those listed at pages 1701 to 1703 of the C.T.F.A. International Cosmetic Ingredient Dictionary and Handbook, $8^{th}$ edition, vol. 2, (2000). In one embodiment, the at least one polyamine compound comprising at least two amino groups is chosen from wheat protein, soy protein, oat protein, collagen, and keratin protein.

In one embodiment, the at least one polyamine compound comprising at least two amino groups is not chosen from proteins and protein derivatives. In one embodiment, the at least one polyamine compound comprising at least two amino groups is not chosen from compounds comprising lysine, compounds comprising arginine, and compounds comprising histidine. In one embodiment, the at least one polyamine compound comprising at least two amino groups is chosen from compounds comprising lysine, compounds comprising arginine, compounds comprising histidine, and compounds comprising hydroxylysine.

In the present invention, the at least one polyamine compound is employed in an amount sufficient to inhibit dyed hair fibers from losing their color during shampooing. Typically, it will be present in an amount of from greater than 0% to 30% by weight, preferably from 5% to 20% by weight, and more preferably from 5% to 10% by weight, based on the weight of the composition as a whole.

In general, non-limiting examples of anionic silicones which may be used in the process of the present invention include silicone carboxylates, silicone phosphates, silicone sulfates, silicone sulfosuccinates, and silicone sulfonates.

Suitable silicone carboxylates may be chosen from water soluble silicone compounds comprising at least one carboxylic acid group, oil soluble silicone compounds comprising at least one carboxylic acid group, water-dispersible silicone compounds comprising at least one carboxylic acid group, and silicone compounds comprising at least one carboxylic acid group which are soluble in organic solvents. In one embodiment, the at least one silicone compound comprising at least one carboxylic acid group further comprises at least one alkoxylated chain, wherein the at least one alkoxy group may be chosen from terminal alkoxy groups, pendant alkoxy groups, and alkoxy groups which are intercalated in the skeleton of the at least one silicone compound. Non-limiting examples of at least one alkoxy group include ethylene oxide groups and propylene oxide groups.

The at least one carboxylic acid group may be chosen from terminal carboxylic acid groups and pendant carboxylic acid groups. Further, the at least one carboxylic acid may be chosen from carboxylic acid groups in free acid form, i.e., —COOH, and carboxylic acid groups in salt form, i.e., —COOM, wherein M may be chosen from inorganic cations, such as, for example, potassium cations and sodium cations, and organic cations.

In one embodiment, the at least one silicone compound comprising at least one carboxylic acid group is chosen from silicone compounds of formula (I) and salts thereof:

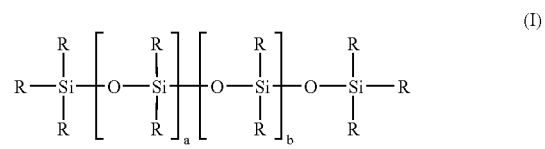

wherein: a is an integer ranging from 1 to 100; b is an integer ranging from 0 to 500; R, which may be identical or different, are each chosen from optionally substituted hydrocarbon groups comprising from 1 to 9 carbon atoms, optionally substituted phenyl groups, and groups of formula (II):

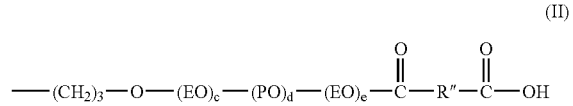

wherein: c, d, and e, which may be identical or different, are each integers ranging from 0 to 20; EO is an ethylene oxide group; PO is a propylene oxide group; and R" is chosen from optionally substituted divalent hydrocarbons, such as alkylene groups and alkenylene groups comprising from 2 to 22 carbon atoms, and optionally substituted divalent aromatic groups, such as groups of formula (III):

and groups of formula (IV):

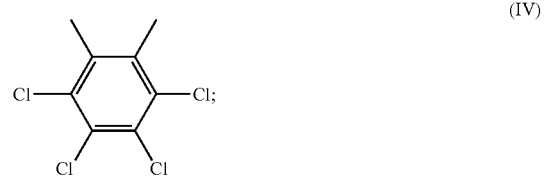

with the proviso that at least one of the R groups is chosen from groups of formula (II) and with the further proviso that when only one of the R groups is chosen from groups of formula (II), the other R groups are not all methyl groups.

Non-limiting examples of the at least one silicone compound include those commercially available from Noveon under the name Ultrasil® CA-1 Silicone and Ultrasil® CA-2 Silicone, both of which correspond to formula (V) below. This silicone carboxylate is sold in the free acid form as an emulsifier and dispersing aid for complexing fatty cationic amines and quaternary amines. Thus, in one embodiment, the at least one silicone compound is chosen from silicone compounds of formula (V) and salts thereof:

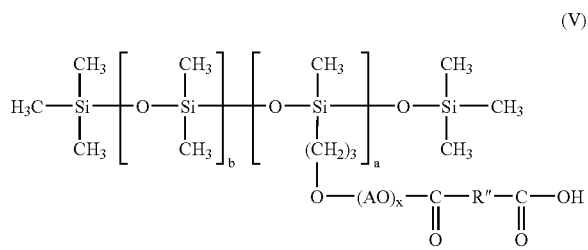

(V)

wherein: a is an integer ranging from 1 to 100; b is an integer ranging from 0 to 500; AO is chosen from groups of formula (VI):

(VI)

wherein: c, d, and e, which may be identical or different, are each integers ranging from 0 to 20; EO is an ethylene oxide group; and PO is a propylene oxide group; x is an integer ranging from 0 to 60; R″ is chosen from optionally substituted divalent hydrocarbons, such as alkylene groups and alkenylene groups comprising from 2 to 22 carbon atoms, and optionally substituted divalent aromatic groups, such as groups of formula (III):

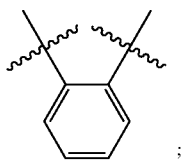

(III)

and groups of formula (IV):

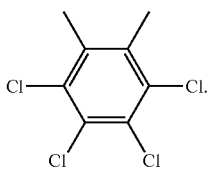

(IV)

Non-limiting examples of the at least one silicone compound include those described in U.S. Pat. Nos. 5,248,783 and 5,739,371, the disclosures of which are incorporated herein by reference, and which are silicone compounds of formula (I).

Suitable silicone phosphates may be chosen from water-soluble silicone compounds comprising at least one phosphate group, oil soluble silicone compounds comprising at least one phosphate group, water-dispersible silicone compounds comprising at least one phosphate group, and silicone compounds comprising at least one phosphate group which are soluble in organic solvents.

In one embodiment, the at least one silicone compound comprising at least one phosphate group further comprises at least one alkoxylated chain, wherein the at least one alkoxy group may be chosen from terminal alkoxy groups, pendant alkoxy groups, and alkoxy groups which are intercalated in the skeleton of the at least one silicone compound. Non-limiting examples of at least one alkoxy group include ethylene oxide groups ("EO"=—CH$_2$—CH$_2$—O—) and propylene oxide groups ("PO"=C$_3$H$_6$O).

The at least one phosphate group may be chosen from terminal phosphate groups and pendant phosphate groups. Further, the at least one phosphate group may be chosen from groups of formula —O—P(O)(OH)$_2$, groups of formula —O—P(O)(OH)(OR), and groups of formula —O—P(O)(OR)$_2$, wherein R may be chosen from H, inorganic cations, and organic cations. Non-limiting examples of inorganic cations include alkali metals, such as, for example, potassium lithium, and sodium. A non-limiting example of organic cations is at least one additional silicone compound which may be identical to or different from the at least one silicone compound bonded to the other oxygen of the phosphate group.

In one embodiment, the at least one silicone compound comprising at least one phosphate group is chosen from silicone compounds of formula (I):

(I)

wherein R$^1$, which may be identical or different, are each chosen from H, organic cations, inorganic cations, optionally substituted hydrocarbons (such as alkyl groups and alkenyl groups comprising from 1 to 22 carbon atoms), optionally substituted aromatic groups; groups of formula (II) and salts thereof:

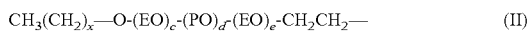

(II)

wherein: c, and d, which may be identical or different, are each integers ranging from 0 to 20; e is an integer ranging from 0 to 19; and x is an integer ranging from 0 to 21; groups of formula (III) and salts thereof:

(III)

wherein: c, d, and e, which may be identical or different, are each integers ranging from 0 to 20; and x is an integer ranging from 0 to 21; and groups of formula (IV) and salts thereof:

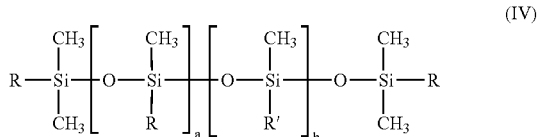

(IV)

wherein: a is an integer ranging from 0 to 200; b is an integer ranging from 0 to 200; R′, which may be identical or different, are each chosen from optionally substituted hydrocarbons, such as alkyl groups and alkenyl groups comprising from 1 to 22 carbon atoms, optionally substituted aromatic groups, groups of formula (III) as defined above and salts thereof; and R, which may be identical or different, are each chosen from optionally substituted hydrocarbons, such as alkyl groups and alkenyl groups comprising from 1 to 22 carbon atoms, optionally substituted aromatic groups, optionally substituted divalent hydrocarbons, such as alkylene groups and alkenylene groups comprising from 1 to 22 carbon atoms, optionally substituted divalent aromatic groups, groups of formula (III) as defined above and salts thereof, and groups of formula (V):

—(EO)$_c$-(PO)$_d$-(EO)$_e$-(CH$_2$)$_3$— (V)

wherein:

the (CH$_2$)$_3$ end is bonded to the silicon of the compound of formula (IV) and the (EO) or (PO) end, if present, is bonded to the oxygen of the compound of formula (I); c, d, and e, which may be identical or different, are each integers ranging from 0 to 20; EO is an ethylene oxide group; and PO is a propylene oxide group; and with the proviso that at least one R is chosen from groups of formula (V) and salts thereof; and with the further proviso that at least one $R^1$ is chosen from groups of formula (IV) and salts thereof and at least one other $R^1$ is chosen from H, organic cations, and inorganic cations.

Non-limiting examples of the inorganic cations include alkali metals, such as potassium, lithium, and sodium. Non-limiting examples of the at least one silicone compound include those commercially available from Phoenix Chemical, Inc. of New Jersey under the name of Pecosil®, such as Pecosil® PS-100, Pecosil® PS-112, Pecosil® PS-150, Pecosil® PS-200, Pecosil® WDS-100, Pecosil® WDS-200, Pecosil® PS-100 B, and Pecosil® PS-100 K and those commercially available from Siltech under the name Silphos A-100 and Silphos A-150. Other non-limiting examples of the at least one silicone compound include those described in U.S. Pat. Nos. 5,070,171, 5,093,452, and 5,149,765 the disclosures of which are incorporated herein by reference.

Suitable silicone sulfates for use in the present invention include those represented by formula VI:

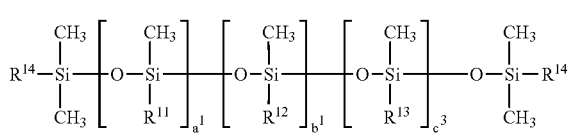
(VI)

wherein $R^{11}$ is selected from lower alkyl having one to eight carbon atoms or phenyl, $R^{12}$ is —(CH$_2$)$_3$—O-(EO)$_x$-(PO)$_y$-(EO)$_z$-SO$_3^{31}$M$^+$ wherein M is a cation and is selected from Na, K, Li, or NH$_4$; x, y and z are integers independently ranging from 0 to 100; $R^{13}$ is —(CH$_2$)$_3$—O-(EO)$_x$-(PO)$_y$-(EO)$_z$-H ; $R^{14}$ is methyl or hydroxyl; $a^1$ and $c^1$ are independently integers ranging from 0 to 50; $b^1$ is an integer ranging from 1 to 50. An example thereof is Ultrasil SA-1 silicone commercially available from Noveon.

Suitable silicone sulfosuccinates which may be employed include, but are not limited to, those corresponding to formula VII:

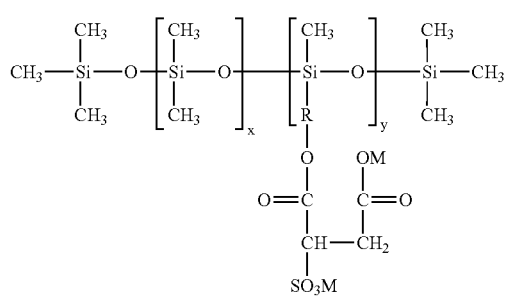
(VII)

wherein R represents a divalent radical selected from

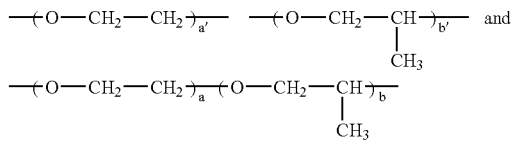

wherein a' and b' range from 0 to 30; x and y are such that the molecular weight ranges from 700 to 1600, and M is an alkali metal such as sodium or potassium, or an ammonium group.

A particularly preferred anionic silicone is Dimethicone PEG-8 phosphate, commercially available from Noveon under the tradename Ultrasil PE-100.

The anionic silicone may be employed in an amount ranging from greater than 0 to 50% by weight, preferably from 5 to 30% by weight, and more preferably from 5 to 15% by weight, based on the weight of the composition as a whole.

The direct dyes that may be used according to the invention are preferably chosen from neutral, acidic or cationic nitrobenzene direct dyes, neutral, acidic or cationic azo direct dyes, quinone direct dyes and in particular neutral, acidic or cationic anthraquinone direct dyes, azine direct dyes, triarylmethane direct dyes, indoamine direct dyes and natural direct dyes.

Among the benzenic direct dyes that may be used according to the invention, mention may be made, in a nonlimiting manner, of the following compounds:

1,4-Diamino-2-nitrobenzene
1-Amino-2-nitro-4-β-hydroxyethylaminobenzene
1-Amino-2-nitro-4-bis(β-hydroxyethyl)aminobenzene
1,4-Bis(β-hydroxyethylamino)-2-nitrobenzene
1-β-Hydroxyethylamino-2-nitro-4-bis(β-hydroxyethylamino)benzene
1-β-Hydroxyethylamino-2-nitro-4-aminobenzene
1-β-Hydroxyethylamino-2-nitro-4-(ethyl)(β-hydroxyethyl)aminobenzene
1-Amino-3-methyl-4-β-hydroxyethylamino-6-nitrobenzene
1-Amino-2-nitro-4-β-hydroxyethylamino-5-chlorobenzene
1,2-Diamino-4-nitrobenzene
1-Amino-2-β-hydroxyethylamino-5-nitrobenzene
1,2-Bis(β-hydroxyethylamino)-4-nitrobenzene
1-Amino-2-tris(hydroxymethyl)methylamino-5-nitrobenzene
1-Hydroxy-2-amino-5-nitrobenzene
1-Hydroxy-2-amino-4-nitrobenzene
1-Hydroxy-3-nitro-4-aminobenzene
1-Hydroxy-2-amino-4,6-dinitrobenzerie
1-β-Hydroxyethyloxy-2-β-hydroxyethylamino-5-nitrobenzene
1-Methoxy-2-β-hydroxyethylamino-5-nitrobenzene
1-β-Hydroxyethyloxy-3-methylamino-4-nitrobenzene
1-β,γ-Dihydroxypropyloxy-3-methylamino-4-nitrobenzene
1-β-Hydroxyethylamino-4-β,γ-dihydroxypropyloxy-2-nitrobenzene
1-β,γ-Dihydroxypropylamino-4-trifluoromethyl-2-nitrobenzene
1-β-Hydroxyethylamino-4-trifluoromethyl-2-nitrobenzene
1-β-Hydroxyethylamino-3-methyl-2-nitrobenzene
1-β-Aminoethylamino-5-methoxy-2-nitrobenzene 1-Hydroxy-2-chloro-6-ethylamino-4-nitrobenzene
1-Hydroxy-2-chloro-6-amino-4-nitrobenzene
1-Hydroxy-6-bis(β-hydroxyethyl)amino-3-nitrobenzene
1-β-Hydroxyethylamino-2-nitrobenzene
1-Hydroxy-4-β-hydroxyethylamino-3-nitrobenzene.

Among the azo direct dyes that may be used according to the invention, mention may be made of the cationic azo dyes described in patent applications WO 95/15144, WO-95/01772 and EP-714 954, the content of which forms an integral part of the invention.

Among azo direct dyes that may also be mentioned are the following dyes, described in the Color Index International 3rd edition:
Disperse Red 17
Acid Yellow 9
Acid Black 1
Basic Red 22
Basic Red 76
Basic Yellow 57
Basic Brown 16
Acid Yellow 36
Acid Orange 7
Acid Red 33
Acid Red 35
Basic Brown 17
Acid Yellow 23
Acid Orange 24
Disperse Black 9.

Mention may also be made of 1-(4'-aminodiphenylazo)-2-methyl-4-bis(β-hydroxyethyl)aminobenzene and 4-hydroxy-3-(2-methoxyphenylazo)-1-naphthalenesulfonic acid.

Among the quinone direct dyes that may be mentioned are the following dyes:
Disperse Red 15
Solvent Violet 13
Acid Violet 43
Disperse Violet 1
Disperse Violet 4
Disperse Blue 1
Disperse Violet 8
Disperse Blue 3
Disperse Red 11
Acid Blue 62
Disperse Blue 7
Basic Blue 22
Disperse Violet 15
Basic Blue 99 and also the following compounds:
1-N-Methylmorpholiniumpropylamino-4-hydroxyanthraquinone
1-Aminopropylamino-4-methylaminoanthraquinone
1-Aminopropylaminoanthraquinone
5-β-Hydroxyethyl-1,4-diaminoanthraquinone
2-Aminoethylaminoanthraquinone
1,4-Bis(β,γ-dihydroxypropylamino)anthraquinone.

Among the azine dyes that may be mentioned are the following compounds:
Basic Blue 17
Basic Red 2.

Among the triarylmethane dyes that may be used according to the invention, mention may be made of the following compounds:
Basic Green 1
Acid Blue 9
Basic Violet 3
Basic Violet 14
Basic Blue 7
Acid Violet 49
Basic Blue 26
Acid Blue 7.

Among the indoamine dyes that may be used according to the invention, mention may be made of the following compounds:
2-β-Hydroxyethylamino-5-[bis(β-4'-hydroxyethyl)amino]anilino-1,4-benzoquinone
2-β-Hydroxyethylamino-5-(2'-methoxy-4'-amino)anilino-1,4-benzoquinone
3-N-(2'-Chloro-4'-hydroxy)phenylacetylamino-6-methoxy-1,4-benzoquinone imine
3-N-(3'-Chloro-4'-methylaminophenylureido-6-methyl-1,4-benzoquinone imine
3-[4'-N-(Ethyl,carbamylmethyl)amino]phenylureido-6-methyl-1,4-benzoquinone imine.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin and apigenidin. It is also possible to use extracts or decoctions containing these natural dyes, and especially henna-based poultices or extracts.

In the event that an oxidative dye is employed, it will typically be in the form of a two-part system containing a lotion formulation which is an aqueous alkaline composition having a pH of from about 7 to 11 having a water content of at least about 70% by weight, a tinctorily effective amount of oxidative dye precursors and at least one anionic or amphoteric surfactant or mixture thereof. The second part, i.e. the developer is an aqueous composition with a pH of from about 2 to about 6, preferably 2 to 3. It contains a peroxide oxidizing agent.

The at least one polyamine having at least two amino groups and the at least one anionic silicone may be present in either the lotion, the developer, both the lotion and the developer, or by itself in a separate container.

The invention also comprises a kit or package of the developer and lotion formulations. A further aspect of this invention is the use of such multi-part systems for the oxidative coloration of hair.

The oxidative dye precursors employed in the practice of this invention comprise one or more primary intermediates together with one or more couplers. The selection of specific intermediates or couplers determines the ultimate color of the treated hair. Such selection is not a critical aspect of the practice of the invention.

A wide variety of primary intermediates can be employed in this invention including, for example: p-phenylenediamine derivatives such as: benzene-1,4-diamine, 2-methyl-benzene-1,4-diamine, 2-chloro-benzene-1,4-diamine, N-phenyl-benzene-1,4-diamine, N-(2-ethoxyethyl)benzene-1,4-diamine, 2-[(4-amino-phenyl)-(2-hydroxy-ethyl)-amino]-ethanol, (2,5-diamino-phenyl)-methanol, 1-(2,5-diamino-phenyl)-ethanol, 2-(2,5-diamino-phenyl)-ethanol, N-(4-aminophenyl)benzene-1,4-diamine, 2,6-dimethyl-benzene-1,4-diamine, 2-isopropyl-benzene-1,4-diamine, 1-[(4-aminophenyl)amino]-propan-2-ol, 2-propyl-benzene-1,4-diamine, 1,3-bis[(4-aminophenyl)(2-hydroxyethyl)amino]propan-2-ol, $N^4,N^4$,2-trimethylbenzene-1,4-diamine, 2-methoxy-benzene-1,4-diamine, 1-(2,5-diaminophenyl)ethane-1,2-diol, 2,3-dimethyl-benzene-1,4-diamine, N-(4-amino-3-hydroxy-phenyl)-acetamide, 2,6-diethylbenzene-1,4-diamine, 2,5-dimethylbenzene-1,4-diamine, 2-thien-2-ylbenzene-1,4-diamine, 2-thien-3-ylbenzene-1,4-diamine, 2-pyridin-3-ylbenzene-1,4-diamine, 1,1'-biphenyl-2,5-diamine, 2-(methoxymethyl)benzene-1,4-diamine, 2-(aminomethyl)benzene-1,4-diamine, 2-(2,5-diaminophenoxy) ethanol, N-[2-(2,5-diaminophenoxy)ethyl]-acetamide, N,N-dimethylbenzene-1,4-diamine, N,N-diethylbenzene-1,4-diamine, N,N-dipropylbenzene-1,4-diamine, 2-[(4-aminophenyl)(ethyl)amino]ethanol, 2-[(4-amino-3-methylphenyl)-(2-hydroxy-ethyl)-amino]-ethanol, N-(2-methoxyethyl)-benzene-1,4-diamine, 3-[(4-aminophenyl)amino]propan-1-ol, 3-[(4-aminophenyl)-amino]propane-1,2-diol, N-{4-[(4-aminophenyl)amino]butyl}benzene-1,4-diamine, and 2-[2-(2-{2-[(2,5-diaminophenyl)oxy]ethoxy}ethoxy)ethoxy]benzene-1,4-diamine;

p-aminophenol derivatives such as: 4-amino-phenol, 4-methylamino-phenol, 4-amino-3-methyl-phenol, 4-amino-2-hydroxymethyl-phenol, 4-amino-2-methyl-phenol, 4-amino-2-[(2-hydroxy-ethylamino)-methyl]-phenol, 4-amino-2-methoxymethyl-phenol, 5-amino-2-hydroxy-benzoic acid, 1-(5-amino-2-hydroxy-phenyl)-ethane-1,2-diol, 4-amino-2-(2-hydroxy-ethyl)-phenol, 4-amino-3-(hydroxymethyl)phenol, 4-amino-3-fluoro-phenol, 4-amino-2-(aminomethyl) phenol, and 4-amino-2-fluoro-phenol; o-aminophenol derivatives such as: 2-amino-phenol, 2,4-diaminophenol, 2-amino-5-methyl-phenol, 2-amino-6-methyl-phenol, N-(4-amino-3-hydroxy-phenyl)-acetamide, and 2-amino-4-methyl-phenol; and heterocyclic derivatives such as: pyrimidine-2,4,5,6-tetramine, 1-methyl-1H-pyrazole-4,5-diamine, 2-(4,5-diamino-1H-pyrazol-1-yl)ethanol, N.sup.2, N.sup.2-dimethyl-pyridine-2,5-diamine, 2-[(3-amino-6-methoxypyridin-2-yl)amino]ethanol, 6-methoxy-N2-methyl-pyridine-2,3-diamine, 2,5,6-triaminopyrimidin-4(1H)-one, pyridine-2,5-diamine, 1-isopropyl-1H-pyrazole-4,5-diamine, 1-(4-methylbenzyl)-1H-pyrazole-4,5-diamine, and 1-(4-chlorobenzyl)-1H-pyrazole-4,5-diamine.

The primary intermediates can be employed in the form of a free base or in the form of an acid additive salt thereof, such as, for example, as a hydrochloride, a hydrobromide, a sulfate or the like.

Suitable couplers include, for example, phenols, resorcinol and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, 7-amino-4-hydroxy-naphthalene-2-sulfonic acid, 2-isopropyl-5-methylphenol, 1,2,3,4-tetrahydro-naphthalene-1,5-diol, 2-chloro-benzene-1,3-diol, 4-hydroxy-naphthalene-1-sulfonic acid, benzene-1,2,3-triol, naphthalene-2,3-diol, 5-dichloro-2-methylbenzene-1,3-diol, 4,6-dichlorobenzene-1,3-diol, and 2,3-dihydroxy-[1,4]naphthoquinone; m-phenylenediamines such as: 2,4-diaminophenol, benzene-1,3-diamine, 2-(2,4-diamino-phenoxy)-ethanol, 2-[(3-aminophenyl)-(2-hydroxy-ethyl)-amino]-ethanol, 2-mehyl-benzene-1,3-diamine, 2-[[2-(2,4-diamino-phenoxy)-ethyl]-(2-hydroxy-ethyl)-amino]-ethanol, 4-{3-[(2,4-diaminophenyl)oxy]propoxy}benzene-1,3-diamine, 2-(2,4-diamino-phenyl)-ethanol, 2-(3-amino-4-methoxy-phenylamino)-ethanol, 4-(2-amino-ethoxy)-benzene-1,3-diamine, (2,4-diamino-phenoxy)-acetic acid, 2-[2,4-diamino-5-(2-hydroxy-ethoxy)-phenoxy]-ethanol, 4-ethoxy-6-methyl-benzene-1,3-diamine, 2-(2,4-diamino-5-methyl-phenoxy)-ethanol, 4,6-dimethoxy-benzene-1,3-diamine, 2-[3-(2-hydroxy-ethylamino)-2-methyl-phenylamino]-ethanol, 3-(2,4-diamino-phenoxy)-propan-1-ol, N-[3-(dimethylamino)phenyl]urea, 4-methoxy-6-methylbenzene-1,3-diamine, 4-fluoro-6-methylbenzene-1,3-diamine, 2-({3-[(2-hydroxyethyl)amino]-4,6-dimethoxyphenyl}amino)ethanol, 3-(2,4-diaminophenoxy)-propan-1,2-diol, 2-[2-amino-4-(methylamino)phenoxy]ethanol, 2-[(5-amino-2-ethoxy-phenyl)-(2-hydroxy-ethyl)-amino]-ethanol, 2-[(3-aminophenyl)amino]ethanol N-(2-aminoethyl)benzene-1,3-diamine, 4-{[(2,4-diaminophenyl)oxy]methoxy}-benzene-1,3-diamine, and 2,4-dimethoxybenzene-1,3-diamine; m-aminophenols such as: 3-amino-phenol, 2-(3-hydroxy-4-methyl-phenylamino)-acetamide, 2-(3-hydroxy-phenylamino)-acetamide, 5-amino-2-methyl-phenol, 5-(2-hydroxy-ethylamino)-2-methyl-phenol, 5-amino-2,4-dichloro-phenol, 3-amino-2-methyl-phenol, 3-amino-2-chloro-6-methyl-phenol, 5-amino-2-(2-hydroxy-ethoxy)-phenol, 2-chloro-5-(2,2,2-trifluoro-ethylamino)-phenol, 5-amino-4-chloro-2-methyl-phenol, 3-cyclopentylamino-phenol, 5-[(2-hydroxyethyl)amino]-4-methoxy-2-methylphenol, 5-amino-4-methoxy-2-methylphenol, 3-(dimethylamino)phenol, 3-(diethylamino)phenol, 5-amino-4-fluoro-2-methylphenol, 5-amino-4-ethoxy-2-methylphenol, 3-amino-2,4-dichlorophenol, 3-[(2-methoxyethyl)amino]phenol, 3-[(2-hydroxyethyl)amino]phenol, 5-amino-2-ethyl-phenol, 5-amino-2-methoxyphenol, 5-[(3-hydroxypropyl)amino]-2-methylphenol, 3-[(3-hydroxy-2-methylphenyl)-amino]propane-1,2-diol, and 3-[(2-hydroxyethyl)amino]-2-methylphenol; and heterocyclic derivatives such as: 3,4-dihydro-2H-1,4-benzoxazin-6-ol, 4-methyl-2-phenyl-2,4-dihydro-3H-pyrazol-3-one, 6-methoxyquinolin-8-amine, 4-methylpyridine-2,6-diol, 2,3-dihydro-1,4-benzodioxin-5-ol, 1,3-benzodioxol-5-ol, 2-(1,3-benzodioxol-5-ylamino)ethanol, 3,4-dimethylpyridine-2,6-diol, 5-chloropyridine-2,3-diol, 2,6-dimethoxypyridine-3,5-diamine, 1,3-benzodioxol-5-amine, 2,6-bis(2-hydroxyethoxy)-3,5-diaminopyridine, 1H-indol-4-ol, 5-amino-2,6-dimethoxypyridin-3-ol, 1H-indole-5,6-diol, 1H-indol-7-ol, 1H-indol-5-ol, 1H-indol-6-ol, 6-bromo-1,3-benzodioxol-5-ol, 2-aminopyridin-3-ol, pyridine-2,6-diamine, 3-[(3,5-diaminopyridin-2-yl)oxy]propane-1,2-diol, 5-[(3,5-diaminopyridin-2-yl)oxy]pentane-1,3-diol, 1H-indole-2,3-dione, indoline-5,6-diol, 3,5-dimethoxypyridine-2,6-diamine, 6-methoxypyridine-2,3-diamine, and 3,4-dihydro-2H-1,4-benzoxazin-6-amine.

Preferred primary intermediates include: p-phenylenediamine derivatives such as: 2-methyl-benzene-1,4-diamine, benzene-1,4-diamine, 1-(2,5-diamino-phenyl)-ethanol, 2-(2,5-diamino-phenyl)-ethanol, N-(2-methoxyethyl)benzene-1,4-diamine, 2-[(4-amino-phenyl)-(2-hydroxy-ethyl)-amino]-ethanol, and 1-(2,5-diaminophenyl)ethane-1,2-diol; p-aminophenol derivatives such as 4-amino-phenol, 4-methylamino-phenol, 4-amino-3-methyl-phenol, 4-amino-2-methoxymethyl-phenol, and 1-(5-amino-2-hydroxy-phenyl)-ethane-1,2-diol; o-aminophenol derivatives such as: 2-amino-phenol, 2-amino-5-methyl-phenol, 2-amino-6-methyl-phenol, N-(4-amino-3-hydroxy-phenyl)-acetamide, and 2-amino-4-methyl-phenol; heterocyclic derivatives such as: pyrimidine-2,4,5,6-tetramine, 1-methyl-1H-pyrazole-4,5-diamine, 2-(4,5-diamino-1H-pyrazol-1-yl)ethanol, and $N^2$, $N^2$-dimethyl-pyridine-2,5-diamine.

Preferred couplers include: phenols, resorcinol and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, and 2-isopropyl-5-methylphenol; m-phenylenediamines such as: benzene-1,3-diamine, 2-(2,4-diamino-phenoxy)-ethanol, 4-{3-[(2,4-diaminophenyl)oxy]propoxy}benzene-1,3-diamine, 2-(3-amino-4-methoxy-phenylamino)-ethanol, 2-[2,4-diamino-5-(2-hydroxy-ethoxy)-phenoxy]-ethanol, and 3-(2,4-diamino-phenoxy)-propan-1-ol; m-aminophenols such as: 3-amino-phenol, 5-amino-2-methyl-phenol, 5-(2-hydroxy-ethylamino)-2-methyl-phenol, and 3-amino-2-methyl-phenol; and heterocyclic derivatives such as: 3,4-dihydro-2H-1,4-benzoxazin-6-ol, 4-methyl-2-phenyl-2,4-dihydro-3H-pyrazol-3-one, 1,3-benzodioxol-5-ol, 1,3-benzodioxol-5-amine, 1H-indol-4-ol, 1H-indole-5,6-diol, 1H-indol-7-ol, 1H-indol-5-ol, 1H-indol-6-ol, 1H-indole-2,3-dione, pyridine-2,6-diamine, and 2-aminopyridin-3-ol.

Most preferred primary intermediates include: p-phenylenediamine derivatives such as: 2-methyl-benzene-1,4-diamine, benzene-1,4-diamine, 2-(2,5-diamino-phenyl)-ethanol, 1-(2,5-diamino-phenyl)-ethanol, and 2-[(4-amino-phenyl)-(2-hydroxy-ethyl)-amino]-ethanol; p-aminophenol derivatives such as: 4-amino-phenol, 4-methylamino-phenol, 4-amino-3-methyl-phenol, and 1-(5-amino-2-hydroxy-phenyl)-ethane-1,2-diol; o-aminophenols such as: 2-amino-phenol, 2-amino-5-methyl-phenol, 2-amino-6-methyl-phenol, and N-(4-amino-3-hydroxy-phenyl)-acetamide; and heterocyclic derivatives such as: pyrimidine-2,4,5,6-tetramine and 2-(4,5-diamino-1H-pyrazol-1-yl)ethanol.

Most preferred couplers include: phenols, resorcinol and naphthol derivatives such as: benzene-1,3-diol, 4-chlorobenzene-1,3-diol, naphthalen-1-ol, 2-methyl-naphthalen-1-ol, and 2-methyl-benzene-1,3-diol; m-phenylenediamine such as: 2-(2,4-diamino-phenoxy)-ethanol, 2-(3-amino-4-methoxy-phenylamino)-ethanol, 2-[2,4-diamino-5-(2-hydroxy-ethoxy)-phenoxy]-ethanol, and 3-(2,4-diamino-phenoxy)-propan-1-ol; m-aminophenols such as: 3-amino-phenol, 5-amino-2-methyl-phenol, 5-(2-hydroxy-ethylamino)-2-methyl-phenol, and 3-amino-2-methyl-phenol; and heterocyclic derivatives such as: 3,4-dihydro-2H-1,4-benzoxazin-6-ol, 4-methyl-2-phenyl-2,4-dihydro-3H-pyrazol-3-one, and 1H-indol-6-ol, and 2-aminopyridin-3-ol.

Surfactants

It may be desirable, in certain circumstances, to employ a surfactant such as, for example, a nonionic surfactant, an anionic surfactant, an amphoteric/zwitterionic surfactant, and a cationic surfactant.

Suitable nonionic surfactants are any suitable nonionic surfactants that have an HLB of from about 3 to about 14. The abbreviation "HLB" stands for hydrophilic lipophilic balance. Examples of suitable nonionic surfactants include, but are not limited to, fatty acid esters and alkoxylated, particularly ethoxylated, fatty acid esters of polyhydric alcohols such as glycerols and sorbitol, for example, polyoxyethylene monolaurate, polyoxyethylene monooleate, polyoxyethylene monostearate, sorbitan monolaurate, sorbitan trioleate, generally with a degree of ethoxylation of from about 20 to about 85; mono- and di-alkanolamides, such as the N-acyl derivatives of mono- and di-ethanol amines, and polyethoxylated monoalkanolamides; amine oxides, such as cocoamidopropyl dimethylamine oxides, coco bis-2-hydroxyethyl amine oxides and lauryl dimmethylamine oxide; ethoxylated alkanolamides; ethoxylated oils and fats such as ethoxylated lanolins; and ethoxylated alkylphenols, such as Nonoxynol.

Suitable anionic surfactants include, for example, the following: the alkali metal, ammonium, or amine salts of alkyl sulfates, alkyl ether sulfates, linear alpha-olefin sulfonates, dialkyl sulfosuccinates, alkylamidosulfosuccinates, and alkyl taurates each having from about $C_{12}$ to $C_{18}$ alkyl or alkenyl groups. Particularly preferred are the salts of lauryl sulfates and lauryl ether sulfates the latter having an average level of ethoxylation of 1-3.

Amphoteric/zwitterionic surfactants belong to the category of surface active chemicals that possess a positive and a negative charge in the same molecule and behave as a cation or an anion depending on the pH of the medium. In general, the positive charge is located on a nitrogen atom while the negative charge is carried by a carboxyl or sulfonate group.

There are a large number of amphoteric surfactants that are suitable for use in this invention. They include, for example, lauryl betaine, lauroamphoglycinate, lauroamphopropylsulfonate, lauroamphopropionate, lauroampho-carboxyglycinate, lauryl sultane, myristamidopropyl betaine, myristyl betaine, myristoamphoglycinate, myristyl propionate, stearoamphoglycinate, stearoamphopropionate, stearoamphopropylsulfonate, stearyl betaine, cocamidoethyl betaine, cocamidopropyl betaine, cocamidopropyl hydroxysultane, cocamidopropyl dimethylamine propionate, cocoamphoglycinate, cocoamphocarboxypropionate, cocoamphocarboxyglycinate, coco-betaine, cocoamphopropionate, cocoamphopropylsulfonate.

The amphoteric surfactants presently preferred for use in this invention are: cocamidopropyl betaine, cocobetaine, stearyl betaine, cocoamphocarboxyglycinate, cocoamphodipropionate, and stearoamphoglycinate.

The lotion may contain organic solvents to assist in dissolving the dye precursors. However, it has been observed that in the compositions of this invention, the organic solvent content should be kept at a minimum. More solvent than is necessary to dissolve the precursors may have the effect of retarding diffusion of the precursors into the hair for reaction. Typically useful solvents include alcohols containing up to three carbon atoms such as ethanol and isopropanol, polyhydroxy alcohols such as propylene or hexylene glycol and lower alkyl ethers thereof such as ethoxy ethers.

Other conventional agents often employed in hair coloring compositions may be employed in the lotion or in the developer. These include, for example, fragrances, coloring agents and chelating agents. Antioxidants such as sodium sulfite erythorbic acid and ascorbic acid may also be included to inhibit premature oxidation.

The oxidizing composition or developer employed in the invention is an acidic aqueous composition which comprises the selected oxidizing agent together with one or more anionic polymers which are insoluble in water.

The preferred oxidizing agent for use in the developer of the invention is hydrogen peroxide although other peroxides may be employed. These include, for example, urea peroxide, melamine peroxide, perborates and percarbonates such as sodium perborate or percarbonate.

The lotion and developer are mixed just before application to the hair. On the hair, they form a stable gel with enough consistency and body to remain on the hair during the complete coloring period without dripping or running. The primary intermediate and coupler, i.e. the dye precursors diffuse rapidly into the hair together with the oxidizing agent. The dyes form within the hair fiber and, since they are large molecules, remain in the hair so that the color change is permanent. The term "permanent" means that the dye does not readily wash out of the hair with ordinary shampoos. The color achieved with the products of this invention is so stable that it may survive as many as 10 shampooings without noticeable change.

Conditioning agents may also be employed in the direct dye and oxidative dye composition(s) so as to impart added conditioning benefits to the composition. The conditioning agents useful in the present invention are those which are dispersible in water and typically may be chosen from cationic surfactants, silicone compounds, polyalkylene glycols and mixtures thereof, preferably mono long-chain ammonium compounds, hydrophilically substituted cationic surfactants, hydrophilically substituted silicone compounds, polyalkylene glycols, and mixtures thereof.

The type of conditioning agent selected depends on the desired characteristics of the product. Highly water soluble conditioning agents are typically used. A combination of conditioning agents is preferably used to provide benefits provided by the different conditioning agents. Conditioning agents which are less water soluble can be used in combination with highly water soluble conditioning agents.

Cationic surfactants may be used as conditioning agents herein. Suitable cationic surfactants useful herein include, but are not limited to, those generally described as mono long-chain ammonium compounds. Nonlimiting examples of such cationic surfactants include: cetyl trimethyl ammonium chloride available, for example, with tradename CA-2350 from Nikko Chemicals and CTAC 30KC available from KCI, stearyl trimethyl ammonium chloride with tradename Arquad 18/50 available from Akzo Nobel, hydrogenated tallow alkyl trimethyl ammonium chloride, stearyl dimethyl benzyl ammonium chloride, stearyl propyleneglycol phosphate dimethyl ammonium chloride, stearoyl amidopropyl dimethyl benzyl ammonium chloride, stearoyl amidopropyl dimethyl (myristylacetate)ammonium chloride, and N-(stearoyl colamino formyl methy)pyridinium chloride.

Also preferred are hydrophilically substituted cationic surfactants in which at least one of the substituents contains one or more aromatic, ether, ester, amido, or amino moieties present as substituents or as linkages in the radical chain. Nonlimiting examples of hydrophilically substituted cationic surfactants useful in the present invention include the materials having the following CTFA designations: quaternium-16, quaternium-26, quaternium-27, quaternium-30, quaternium-33, quaternium-43, quaternium-52, quaternium-53, quaternium-56, quaternium-60, quaternium-61, quaternium-62, quaternium-70, quaternium-71, quaternium-72, quaternium-75, quaternium-76 hydrolyzed collagen, quaternium-77, quaternium-78, quaternium-79 hydrolyzed collagen, quaternium-79 hydrolyzed keratin, quaternium-79 hydrolyzed milk protein, quaternium-79 hydrolyzed silk, quaternium-79 hydrolyzed soy protein, and quaternium-79 hydrolyzed wheat protein, quaternium-80, quaternium-81, quaternium-82, quaternium-83, quaternium-84, and mixtures thereof.

Highly preferred hydrophilically substituted cationic surfactants include dialkylamido ethyl hydroxyethylmonium salt, dialkylamidoethyl dimonium salt, dialkyloyl ethyl hydroxyethylmonium salt, dialkyloyl ethyldimonium salt, alkyl amidopropyl trimonium salt, polyoxyethylene alkyl ammonium salt, and mixtures thereof; for example, commercially available under the following tradenames; VARISOFT 110, VARISOFT PATC, VARIQUAT K1215 and 638 from Witco Chemical, ETHOQUAD 18/25, ETHOQUAD O/12PG, ETHOQUAD C/25, and ETHOQUAD S/25 from Akzo, DEHYQUART SP from Cognis, and MONAQUAT ISEIS, and MONAQUAT SL-5 available from Uniqema.

The polyalkylene glycols useful herein as conditioning agents include those which are soluble or dispersible in water. Polyethylene glycols are preferred.

Polyalkylene glycols having a molecular weight of more than about 100 are useful herein. Ethylene oxide polymers are preferred in view of their generally good water solubility, dispersibility, and transparency. Polyethylene-polypropylene glycols and polyoxyethylene-polyoxypropylene copolymer polymers having good dispersibility and transparency may also be useful. In the above structure, x3 has an average value of from about 4 to about 600, preferably from about 6 to about 120, and more preferably from about 10 to about 40.

The composition(s) of the present invention may also comprise additives, for instance those chosen from the non-exhaustive list such as reducing agents, antioxidants, sequestering agents, softeners, antifoams, moisturizers, emollients, basifying agents, plasticizers, sunscreens, direct dyes or oxidation dyes, pigments, mineral fillers, clays, colloidal minerals, nacres, nacreous agents, fragrances, peptizers, preserving agents, fixing or non-fixing polymers, proteins, vitamins, antidandruff agents, aliphatic or aromatic alcohols, and more particularly ethanol, benzyl alcohol, modified or unmodified polyols, such as glycerol, glycol, propylene glycol, dipropylene glycol, butylene glycol or butyl diglycol, volatile silicones, mineral, organic or plant oils, oxyethylenated or non-oxyethylenated waxes, paraffins, fatty acids, associative or non-associative thickening polymers, fatty amides, fatty esters, fatty alcohols, and the like.

The method of the invention comprises applying the dye (direct or oxidative) to the hair to be colored and allowing it to remain in contact with the hair until the desired hair color has been attained after which the composition is removed from the hair.

The present invention will be better understood from the examples which follow, all of which are intended for illustrative purposes only and are not meant to unduly limit the scope of the invention in any way.

EXAMPLES

Bleached hair swatches were dyed with a coloration composed solely of basic/Arianor or chromatic dyes. The chromatic coloration, Redken Color Fusion Hi-Fusion R, was mixed in a 1:1 ratio with Redken Pro-oxide 20 volume Cream Developer and remained on the hair for 30 minutes, whereas the basic coloration, Matrix Prizms Light Auburn, was applied as is and remained on the hair for 20 minutes. Swatches were rinsed with warm water for 25 seconds. In another set of hair swatches, the Polyamine/Amionic Silicone was added to the color cream prior to application to hair. Following the coloring process, the initial L*a*b* value of the colored hair swatches were obtained. The swatches were shampooed seven consecutive times with a 15% SLES-2 solution (pH 6.35). Specifically, 0.4g of SLES-2 solution per 1 g of hair was applied, massaged into the swatch for 15 seconds, and rinsed with warm water for 10 seconds. After at least 7 shampoos, the swatches were blown dry and the final L*a*b* values were obtained. The ΔE* value, representing the total color change was calculated using the following formula:

$$\Delta E^* = [(\Delta a^*)^2 + (\Delta b^*)^2 + (\Delta c^*)^2]^{1/2}$$

Swatches were treated in triplicate with one of the following colorations:

A: Coloration without PEI/Silicone Phosphate

B: Coloration with 1.0% PEI and 0.5% Dimethicone PEG-8 Phosphate

C: Coloration with 3.0% PEI and 0.5% Dimethicone PEG-8 Phosphate

D: Coloration with 5.0% PEI and 0.5% Dimethicone PEG-8 Phosphate

All reported concentrations are percent active rather than as is.

After 1 dye out and at least 7 shampoos, statistically significant improvement in color retention was observed for swatches that were dyed with mixtures B, C, and D compared with those swatches dyed with the coloration without PEI/Silicone Phosphate (A). Table I displays the resulting ΔE* values.

TABLE I

Change in Total Color After 7 Shampoos

| Coloration | Treatment | ΔE* Value |
| --- | --- | --- |
| Chromatic | A | 20.54 |
| | B | 16.52 |
| | C | 13.32 |
| | D | 10.84 |
| Basic/Arianor | A | 16.37 |
| | B | 12.52 |
| | C | 13.55 |
| | D | 13.55 |

What is claimed is:

1. A process for dyeing hair fibers in a manner which inhibits color loss during shampooing comprising contacting the hair fibers with a composition containing:
   (a) at least one polyamine having at least two amino groups;
   (b) at least one anionic silicone; and
   (c) at least one dye component chosen from a direct dye and an oxidative dye.

2. The process of claim 1 wherein (a) is present in the composition in an amount of from greater than 0% to about 30% by weight, based on the weight of the composition.

3. The process of claim 1 wherein (a) is present in the composition in an amount of from about 5 to about 10% by weight, based on the weight of the composition.

4. The process of claim 1 wherein (a) is a polyethylene imine.

5. The process of claim 1 wherein (a) is a polyvinyl amine.

6. The process of claim 1 wherein (b) is a silicone phosphate.

7. The process of claim 1 wherein (b) is present in the composition in an amount of from greater than 0% to about 50% by weight, based on the weight of the composition.

8. The process of claim 1 wherein (c) is a direct dye.

9. The process of claim 1 wherein (c) is an oxidative dye.

10. A composition for dyeing hair in a manner which inhibits color loss during shampooing comprising:
    (a) at least one polyamine having at least two amino groups;
    (b) at least one anionic silicone; and
    (c) at least one dye component chosen from a direct dye and an oxidative dye.

11. The composition of claim 10 wherein (a) is present in the composition in an amount of from greater than 0% to about 30% by weight, based on the weight of the composition.

12. The composition of claim 10 wherein (a) is present in the composition in an amount of from about 5 to about 10% by weight, based on the weight of the composition.

13. The composition of claim 10 wherein (a) is a polyethylene imine.

14. The composition of claim 10 wherein (a) is a polyvinyl amine.

15. The composition of claim 10 wherein (b) is present in the composition in an amount of from greater than 0% to about 50% by weight, based on the weight of the composition.

16. The composition of claim 10 wherein (c) is a direct dye.

17. The composition of claim 10 wherein (c) is an oxidative dye.

18. A kit for dyeing hair comprising:
    (a) at least one unit containing a hair dyeing lotion;
    (b) at least one unit containing a hair dyeing developer;
    (c) at least one polyamine having at least two amino groups contained in (a) and/or (b); and
    (d) at least one anionic silicone present in (a) and/or (b).

19. A kit for dyeing hair comprising:
    (a) at least one unit containing a hair dyeing lotion;
    (b) at least one unit containing a hair dyeing developer; and
    (c) at least one unit containing (i) at least polyamine having at least two amino groups and (ii) at least one anionic silicone.

* * * * *

UNITED STATES PATENT AND TRADEMARK OFFICE
CERTIFICATE OF CORRECTION

PATENT NO. : 7,449,029 B2  Page 1 of 1
APPLICATION NO. : 11/280372
DATED : November 11, 2008
INVENTOR(S) : Nghi Van Nguyen et al.

It is certified that error appears in the above-identified patent and that said Letters Patent is hereby corrected as shown below:

On the title page in the title, delete "COLOR" and insert --COLORING--.
On the title page, after (73) Assignee, delete "L'Oreal (FR)" and insert --L'Oréal (FR)--.
Column 1, line 1, delete "COLOR" and insert --COLORING--.
Column 18, line 34, after "(i) at least" insert --one--.

Signed and Sealed this

Sixth Day of April, 2010

David J. Kappos
*Director of the United States Patent and Trademark Office*